(12) United States Patent
Osgood et al.

(10) Patent No.: US 6,441,379 B1
(45) Date of Patent: Aug. 27, 2002

(54) IMAGING SYSTEM FOR AN OPTICAL SCANNER

(75) Inventors: Avery Osgood, Bellingham; Mack Schermer, Belmont, both of MA (US)

(73) Assignee: Packard Bioscience Corporation, Meriden, CT (US)

( * ) Notice: Subject to any disclaimer, the term of this patent is extended or adjusted under 35 U.S.C. 154(b) by 0 days.

(21) Appl. No.: 09/356,428

(22) Filed: Jul. 19, 1999

Related U.S. Application Data

(63) Continuation-in-part of application No. 09/258,484, filed on Feb. 26, 1999.

(51) Int. Cl.⁷ .............................................. G01N 21/64
(52) U.S. Cl. ................................ 250/458.1; 250/216
(58) Field of Search ........................... 250/458.1, 216

(56) References Cited

U.S. PATENT DOCUMENTS

| | | | |
|---|---|---|---|
| 4,122,348 A | 10/1978 | Bruck | 250/461 |
| 4,407,008 A * | 9/1983 | Schmidt et al. | 358/93 |
| 5,022,757 A | 6/1991 | Modell | 356/318 |
| 5,329,461 A | 7/1994 | Allen et al. | 364/497 |
| 5,381,224 A | 1/1995 | Dixon et al. | 356/72 |
| 5,399,866 A | 3/1995 | Feldman et al. | 250/458 |
| 5,631,734 A | 5/1997 | Stern et al. | 356/317 |
| 5,672,880 A | 9/1997 | Kain | 250/458.1 |
| 5,719,391 A | 2/1998 | Kain | 250/235 |
| 6,121,603 A * | 9/2000 | Hang et al. | 250/216 |

FOREIGN PATENT DOCUMENTS

| | | | | |
|---|---|---|---|---|
| DE | 3821422 A1 | 1/1989 | | G01N/21/88 |
| DE | 19842153 A1 | 3/2000 | | G02B/21/00 |
| JP | 10096862 | 4/1998 | | G02B/21/06 |

* cited by examiner

*Primary Examiner*—Constantine Hannaher
*Assistant Examiner*—Otilia Gabor
(74) *Attorney, Agent, or Firm*—Cesari and McKenna, LLP

(57) ABSTRACT

An imaging system comprises a radiation device for providing excitation radiation of at least two different wavelengths, an objective lens for focusing the excitation wavelengths onto a sample to produce fluorescent emission, and a mirror, configured as a geometric beam splitter, disposed in the transmission path of the emission radiation and excitation radiation subsequent to reflection from the sample and collimation by the lens, wherein the mirror is utilized to reflect one of the collimated excitation and emission radiation such that the emission is directed to a detector and the collimated excitation is directed away from the detector.

23 Claims, 3 Drawing Sheets

IMAGING SYSTEM FOR AN OPTICAL SCANNER

CROSS REFERENCE TO RELATED APPLICATION

This application is a continuation-in-part of commonly-assigned patent application 09/258,484 filed Feb. 26, 1999.

BACKGROUND OF THE INVENTION

1. Field of the Invention

This invention in general relates to optical scanning systems and, in particular, to scanning systems such as fluorescent microarray readers, DNA micro-array readers, or "bio-chip" readers, in which excitation radiation of various wavelengths are used to produce fluorescence in a scanned sample.

2. Description of the Prior Art

The use of excitation radiation to produce fluorescence in a scanned sample is known. U.S. Pat. No. 5,381,224 issued to Dixon et al. discloses scanning optical imaging systems for macroscopic specimens, the system allowing both confocal and non-confocal imaging to be performed in reflected light. Fluorescent imagers are used to acquire data in experiments that utilize fluorescent labels to identify the state of a sample being tested. In some cases the presence of or lack of fluors in the sample determines the experimental result. In other cases the density of the fluors, a function of the intensity of the radiation emitted from the sample, is the measurement of interest and the experimental result can be inferred by measuring the intensity of the detected radiation.

An example of a process that uses fluorescent labels is the microarray. A microarray is a set of experiments involving DNA (or RNA) bound to a glass substrate. Reference or "target" DNA is spotted onto a glass substrate—typically a one- by three-inch glass microscope slide—where it chemically binds to the surface. Each spot, or sample, of DNA constitutes a separate experiment. "Probe" DNA or RNA which has been labeled with a fluorophor is then introduced to the surface of the slide and is allowed to hybridize with the target DNA. Excess probe DNA that does not bind with target DNA is removed from the surface of the slide in a subsequent washing process.

The experiment allows the binding affinity between the probe and target DNA to be measured to determine the likeness of their molecular structures; complementary molecules have a much greater probability of binding than unrelated molecules. The probe DNA is labeled with fluorescent labels that emit a range of radiation energy centered about and including a wavelength $\lambda_{emission}$ when excited by an external radiation source of a shorter wavelength $\lambda_{excitation}$. The brightness of emitted radiation is a function of the fluor density in the illuminated sample. Because the fluor density is a function of the binding affinity or likeness of the probe molecule to the target molecule, the brightness of each sample can be mapped as to the degree of similarity between the probe DNA and the target DNA present. On a typical microarray up to tens of thousands of experiments can be performed simultaneously on the probe DNA, allowing for a detailed characterization of complex molecules.

A scanning fluorescent imager divides the area of interest into a set of discrete image elements referred to as pixels. Each pixel is independently addressed and measured for the presence of fluors. The fluors are excited by an incident excitation beam and a portion of the resulting emitted fluorescence radiation is collected and measured by detection apparatus. Each measurement results in a data point that represents the relative fluor density of the measured pixel. The pixel data is then reconstructed to create a quantified representation of the area scanned.

In a scanning microscope, each pixel is illuminated independently while it is being addressed. The light source is typically a single-wavelength laser device focused down to form a spot of the desired size. Radiation is emitted by the fluors in an outward, hemispherical transmission pattern. A portion of this emitted radiation is collected by beam collection optics and directed to the detection apparatus. Additional radiation collected is radiation from the incident excitation beam which is reflected or scattered by the surface of the sample. The imager optics must discriminate between the two radiation wavelengths by rejecting the excitation radiation and passing the fluorescent radiation. Optical filtering components, such as dichroic and band pass filters, provide the discrimination in conventional systems.

Laser fluorescence micro-array scanners incorporate the ability to deliver multiple laser excitation wavelengths so that fluorescence data can be obtained from the sample at two or more emission wavelengths by detecting two or more fluorescent dyes. Such a unique excitation and emission wavelength pair is typically referred to as a "Channel". Many DNA micro-array samples utilize a two-wavelength scanning method, where the results of one wavelength scan are used as control values and the results of the other wavelength scan represent the desired experimental result, as in Differential Gene Expression. As the market and application mature, and a larger variety of suitable dyes become available, the demand for alternative excitation wavelengths and emission bands will increase.

Most scanning confocal microscopes employ a dichroic or multichroic beam splitter for color separation between the excitation radiation wavelength $\lambda_{excitation}$ and the emission radiation wavelength $\lambda_{emission}$. U.S. Pat. No. 5,672,880 issued to Kain, for example, discloses a fluorescence imaging system in which fluorescent light emitted by a sample is collected by an objective and passed through a dichroic filter placed along the optical axis between a laser and the objective to direct the fluorescent light onto a photodetector. Dichroic beam splitters are fabricated using a vacuum deposition process in which inorganic crystalline materials having varying indices of optical refraction are deposited in layers onto optical substrates to create optical filters with specific band-pass and/or band-reject characteristics.

In practice, an optical scanning system may operate utilizing five or more single-wavelength radiation devices producing ten or more unique, but variable, emission bands. These operating parameters impose a specification requirement that the component multichroic optical element be designed so as to reflect all five wavelengths and pass the emission wavelengths. A first drawback to this approach is that such a beam splitter specification may be quite difficult to achieve in practice. Moreover, future improvements and developments in optical scanning systems may necessitate that the systems operate with even more excitation and emission wavelengths, requiring a multichroic beam splitter having an even more demanding specification requirements.

Another drawback of conventional optical scanning systems is the design complexity incurred by the use of single-wavelength radiation devices. By utilizing one or more multi-wavelength radiation devices, with an appropriate wavelength selection device, a more compact, robust optical scanning system can be achieved.

While the art describes a variety of imaging systems for optical scanning, there remains a need for improvements that offer advantages and capabilities not found in presently available scanners, and it is a primary object of this invention to provide such improvements.

It is another object of the present invention to provide an imaging system which can image a sample utilizing two or more different wavelengths of excitation radiation on a single microarray sample.

It is yet another object of the present invention to provide an imaging system which utilizes excitation devices producing two or more wavelengths of radiation.

It is further an object of the present invention to provide an optical scanning system which can be adapted for use with newly-available fluors without incurring the need to reconfigure the imaging system.

Other objects of the invention will be obvious, in part, and, in part, will become apparent when reading the detailed description to follow.

SUMMARY OF THE INVENTION

The present invention discloses an imaging system comprising a radiation device providing excitation radiation of different wavelengths, an objective lens for focusing the excitation radiation onto a sample to produce fluorescent emission, and a mirror, configured as a geometric beam splitter, disposed in the transmission path of the emission radiation and excitation radiation subsequent to reflection from the sample and collimation by the lens, the mirror reflecting one of the collimated excitation and emission radiation such that the emission is directed to a detector and the collimated excitation is directed away from the detector. Other features of the invention will be readily apparent when the following detailed description is read in connection with the drawings.

BRIEF DESCRIPTION OF THE DRAWINGS

The structure and operation of the invention, together with other objects and advantages thereof, may best be understood by reading the detailed description to follow in connection with the accompanying drawings, of which.

DETAILED DESCRIPTION OF ILLUSTRATIVE EMBODIMENTS

Figure 1:
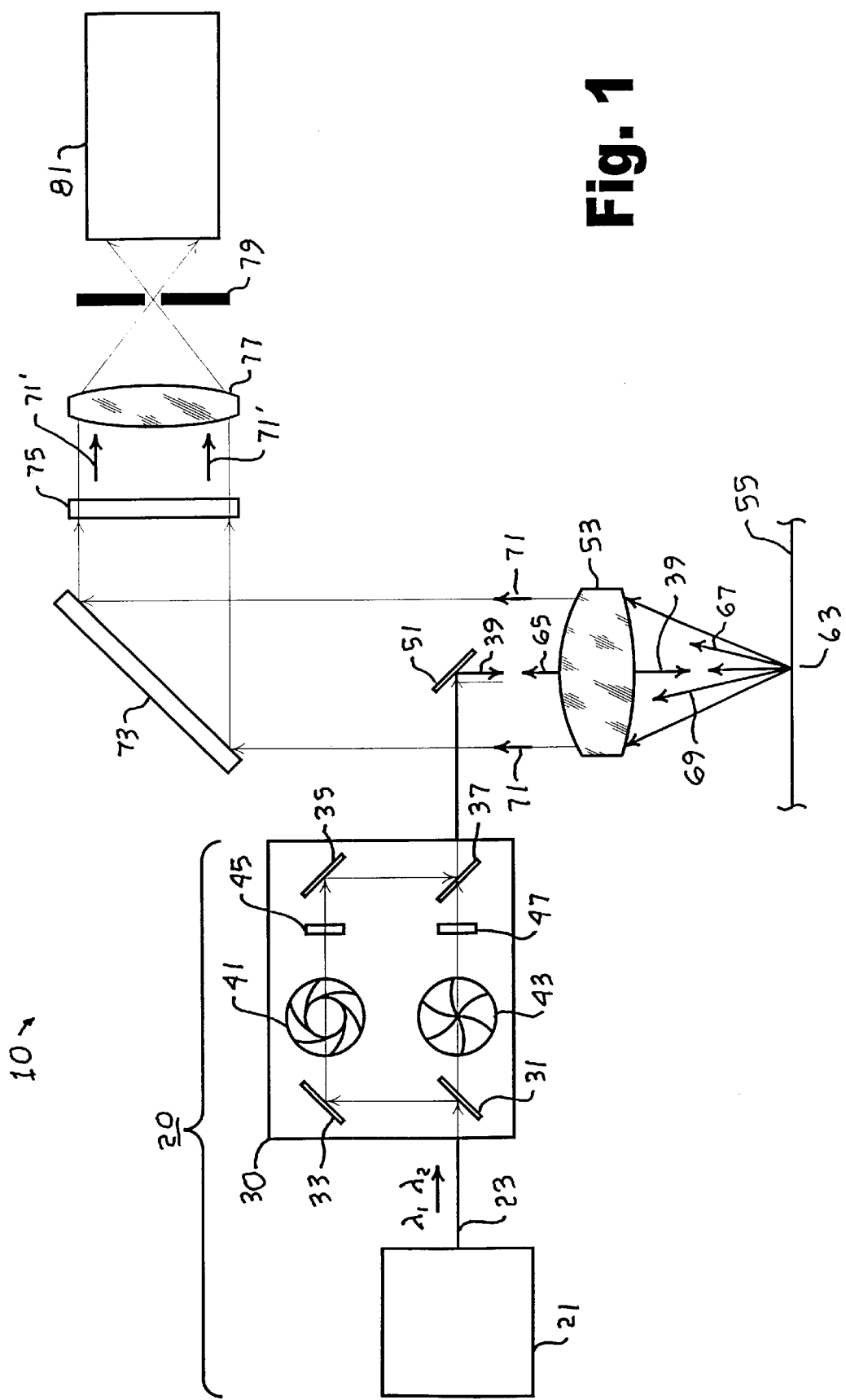
FIG. 1 is a diagrammatic illustration of a preferred embodiment of an imaging system in accordance with the present invention, the imaging system comprising an excitation radiation device, an objective lens, and a mirror utilized for reflecting excitation radiation to and from the sample and away from the detector.

There is shown in FIG. 1 a diagrammatical representation of an imaging system 10, in accordance with the present invention, as can be utilized in the analysis of a sample 55. Imaging system 10 includes an illumination head 20 comprising a shutter assembly 30 and an excitation radiation device 21. The excitation radiation device 21 may be a broadband radiation device or a multi-wavelength laser device such as exemplified by the Spectra-Physics Model 161C laser which provides output radiation at 514 nm, 488 nm, and 458 nm. In a preferred embodiment, the excitation radiation device 21 provides radiation comprising two wavelengths $\lambda_1$ and $\lambda_2$, such as 514 nm and 488 nm, to the shutter assembly 30 via an optical fiber cable 23. The shutter assembly 30 selects one of the excitation wavelengths at a time for illumination of the sample 55. For purpose of illustration, radiation of wavelength $\lambda_1$ has been selected for output from the shutter assembly 30.

The shutter assembly 30 comprises a first beam splitter 31 which is highly reflective to radiation of wavelength $\lambda_1$ and highly transmissive to radiation of wavelength $\lambda_2$. Radiation of wavelength $\lambda_1$ reflected from the first beam splitter 31 to follow a first transmission path through a first shutter 41, and radiation of wavelength $\lambda_2$ is transmitted through the first beam splitter 31 to follow a second transmission path through a second shutter 43. Radiation of wavelength $\lambda_1$, following the first transmission path, is reflected again at a first mirror 33, which is highly reflective to $\lambda_1$ radiation. The $\lambda_1$ radiation reflected from the first mirror 33 passes through the first is shutter 41, here shown as open, passes through a first narrow pass filter 45, reflects from a second mirror 35, and reflects from a second beam splitter 37. The second beam splitter 37 is highly reflective to $\lambda_1$ radiation and is highly transmissive to $\lambda_2$ radiation. After reflection from the second beam splitter 37, the $\lambda_1$ radiation is output from the shutter assembly 30 as excitation radiation 39.

Radiation of wavelength $\lambda_2$ is transmitted along the second transmission path through the first beam splitter 31 to the second shutter 43, here shown as closed. When the second shutter 43 is open, $\lambda_2$ radiation passes through a second narrow pass filter 47 and through the second beam splitter 37. When the first shutter 41 is closed, $\lambda_2$ radiation is output (not shown) from the shutter assembly 30 as the excitation radiation 39.

The excitation radiation 39 is emitted from the shutter assembly 30 and reflected to the surface of the sample 55 by an excitation mirror 51. An objective lens 53 is positioned between the excitation mirror 51 and the surface of sample 55 so as to focus the excitation beam 39 to a desired spot size 63 on the surface of the sample 55. In the preferred embodiment, the effective focal length of the objective lens 53 is approximately 6 millimeters. This provides a spot size of about 5 $\mu$m from an excitation radiation beam 0.6 millimeter in diameter.

When projected onto the surface of the sample 55, the excitation radiation 39 produces three types of radiation which emanate from the surface of the sample 55. The first type of radiation, a specular reflection beam 65 having wavelength of $\lambda_1$, results from the reflection of a portion of the incident excitation radiation 39 along a path normal to the surface of the sample 55 (i.e., back along the incident path of transmission). The second type of radiation, a diffuse reflection 67, also of wavelength $\lambda_1$, is that portion of the excitation radiation 39 reflected from the surface of the sample 55 in an other than normal direction. The reflection path of the diffuse reflection 67 is not confined to the diameter of the incident path of transmission of the excitation radiation 39 because the diffuse reflection 67 is substantially scattered by the surface.

The third type of radiation, an emission radiation 69, is produced by the illumination of fluors in the sample 55 in response to the incident excitation radiation 39. As is well known in the relevant art, such fluors emit when excited by radiation of the proper wavelength. Thus, when illuminated by radiation of wavelength $\lambda_1$ the fluors in the sample 55 produce radiation of wavelength $\lambda_{emit1}$, typically 20 to 40 nm longer than the wavelength $\lambda_1$ of the excitation radiation 39. By way of comparison, the energy of the excitation radiation 39 at the surface of sample 55 is on the order of 1 mW, and the energy of the emission radiation 69 is on the order of $10^{-11}$ watts. As can be appreciated by one skilled in the relative art, the signal-to-noise ratio of the emitted power to the excitation power decreases as the size of the specular reflection beam 65 increases and as the amount of the diffuse reflection 67 emanating from the surface of sample 55 increases.

The specular reflection beam 65 and those portions of the diffuse reflection 67 and the emission radiation 69 incident on the sample side of the objective lens 53 are collimated into a composite emission beam 71 comprising radiation of wavelengths $\lambda_1$ and $\lambda_{emit1}$. The numerical aperture (NA) of the objective lens 53 is at least 0.5, and is made as large as practical so as to intercept the greatest portion of the emission radiation 69, thus to improve the accuracy of the detection process, as explained in greater detail below. In a preferred embodiment, the objective lens 53 has a numerical aperture of about 0.75.

The composite emission beam 71 is transmitted to a detector 81. An optional broadband mirror 73 may be used to provide a folded transmission path by reflection of the incident composite emission beam 71. By utilizing the broadband mirror 73, the cross-sectional profile of the imaging system 10 can be advantageously reduced. The detector 81 is preferably a photo-multiplier tube, but an avalanche photodiode or a solid state optical detection device can be used in the alternative. The photo-multiplier tube is preferable because of its high sensitivity and adjustable gain. Moreover, the output of the photo-multiplier tube comprises a current that is proportional to the detected radiation power. This current signal can be filtered and then converted to a digital value using an analog-to-digital converter.

A detector filter 75, substantially transmissive to the emission radiation 69 and substantially non-transmissive to the excitation radiation 39, may be disposed in the transmission path of the composite emission beam 71 between the objective lens 53 and the detector 81. The detector filter 75 may comprise either a band pass filter or a long pass filter. The detector filter 75 serves to attenuate most or all of the diffuse reflection 67 such that a filtered emission beam 71", comprising primarily the emission radiation 69 of wavelength $\lambda_{emit}$, is transmitted to the detector 81. In an alternative embodiment, a focusing lens 77 and an aperture stop 79 may be positioned in the transmission path of filtered emission beam 71" as shown. When used in the imaging system 10, the focusing lens 77 forms a confocal system with the objective lens 53 and images the filtered emission beam 71" onto the detector 81. As can be appreciated by one skilled in the relevant art, there may be provided additional band pass or long pass filters for each excitation and emission wavelength pair utilized in the imaging system 10.

The disclosed embodiments advantageously utilize geometric beam splitting and thereby demonstrate an advantages over conventional dichroic and multichroic beam splitting methods and apparatuses. Where dichroics comprise a glass element designed to reflect particular wavelengths and to transmit others, a geometric beam splitter as utilized in the imaging system 10 disclosed comprises the excitation mirror 51. The excitation is mirror 51 is designed to reflect the excitation radiation 39 to the surface of the sample 55 and to reflect the specular reflection beam 65 from the surface of the sample 55, and is physically sized to allow the detector 81 to receive the maximum amount of the emission radiation 69. The excitation mirror 51 has a major dimension larger than the width of the excitation beam 39 and is placed about 45° with respect to the transmission path of the excitation beam 39. When properly aligned, the excitation mirror 51 will intercept and redirect substantially all the specular reflection 65 to the shutter assembly 30 and away from the detector 81, thus improving the system signal-to-noise ratio.

Figure 2:
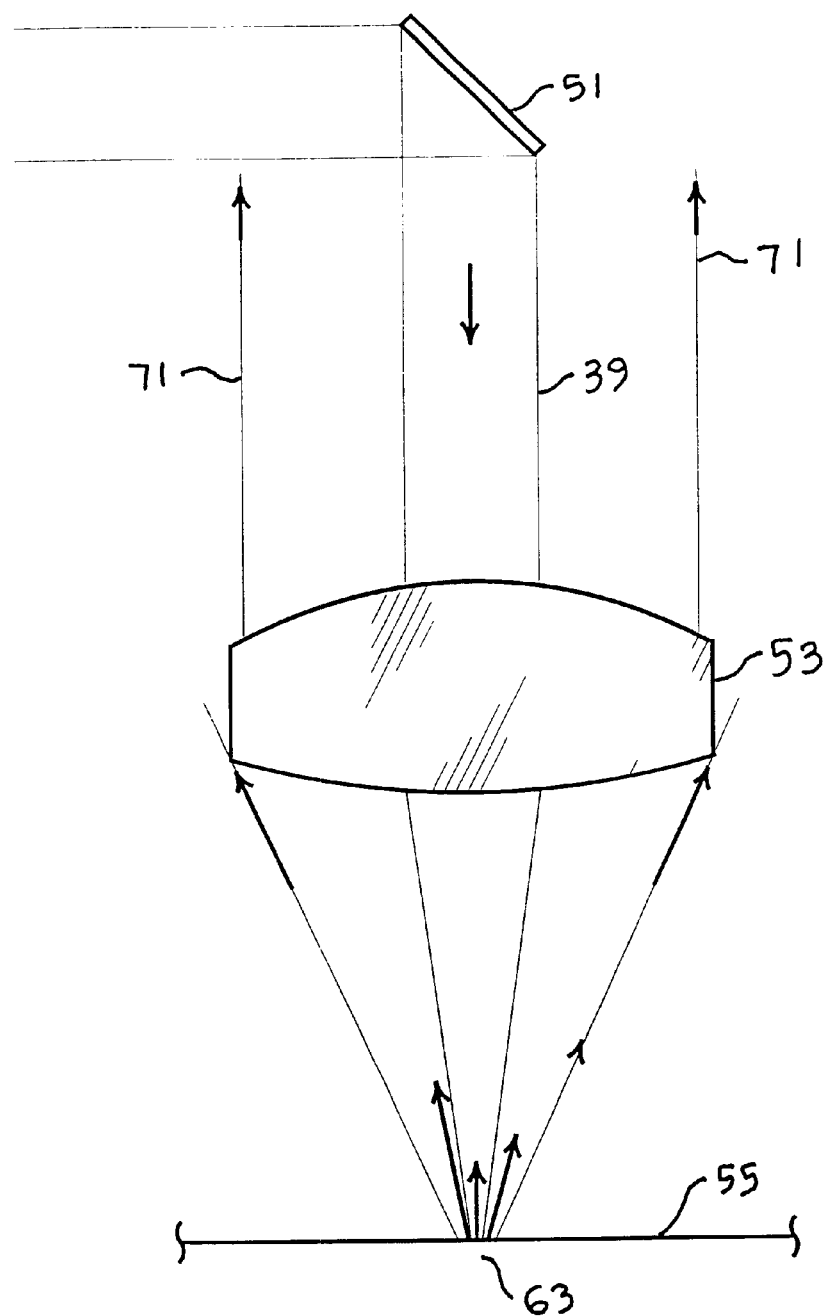
FIG. 2 is a cross-sectional diagram of the objective lens and mirror of FIG. 1, showing the relationship between emission beam width, excitation beam width, and the size of the mirror.

The relationship of the numerical aperture of the objective lens 53 to a geometric emission transmission factor (GETF) can be best explained with reference to FIG. 2. GETF is defined as the ratio of: i) the blockage of the composite emission beam 71 resulting from placement of the mirror 51 (and associated mounting components) in the transmission path, and ii) the overall path diameter of the composite emission beam 71. It can be shown, with the following two examples, that a higher numerical aperture will improve the GETF of a particular imaging system.

In the first example, we specify a spot size 63 of approximately 5 $\mu$m on the surface of the sample 55 with the excitation radiation 39 having a beam diameter of 0.6 millimeter. This can be achieved if the objective lens 53 has an effective focal length of about 6 millimeters. For an NA of 0.75, the aperture diameter is about 13.6 millimeters to give an aperture area of about 145.26 mm. If the excitation mirror 51 and any associated mounting (not shown) have a diameter of 3.17 mm and are set at a 45° angle with respect to the transmission path of the composite emission beam 71, the cross-sectional area of blockage is about 5.57 mm². With this configuration, the GETF is found to be:

$$GETF = \frac{145.26 \text{ mm}^2}{5.57 \text{ mm}^2} = 26.07$$

In the second example, the objective lens 53 has an effective focal length of 10 millimeters and an NA of 0.30. The aperture diameter is about 6.2 millimeter to give an aperture area of about 30.19 mm². To produce a 5 $\mu$m excitation spot, the input excitation radiation 39 should comprise a beam of about 1.0 millimeter in diameter. If the excitation mirror 51 has a diameter of 2.0 millimeter, the excitation radiation 39 will be completely intercepted, even allowing for some tolerance in position. If the excitation mirror 51 is set at a 45° angle with respect to the transmission path, the area of blockage is about 2.22 mm². With this configuration, the GETF is found to be:

$$GETF = \frac{30.19 \text{ mm}^2}{2.22 \text{ mm}^2} = 13.06$$

That is, the GETF is reduced by a factor of two in the second configuration, demonstrating that the GETF is a function of both lens NA and effective focal length. The excitation spot size is related to the effective focal length and the emission aperture is related to the NA.

Figure 3:
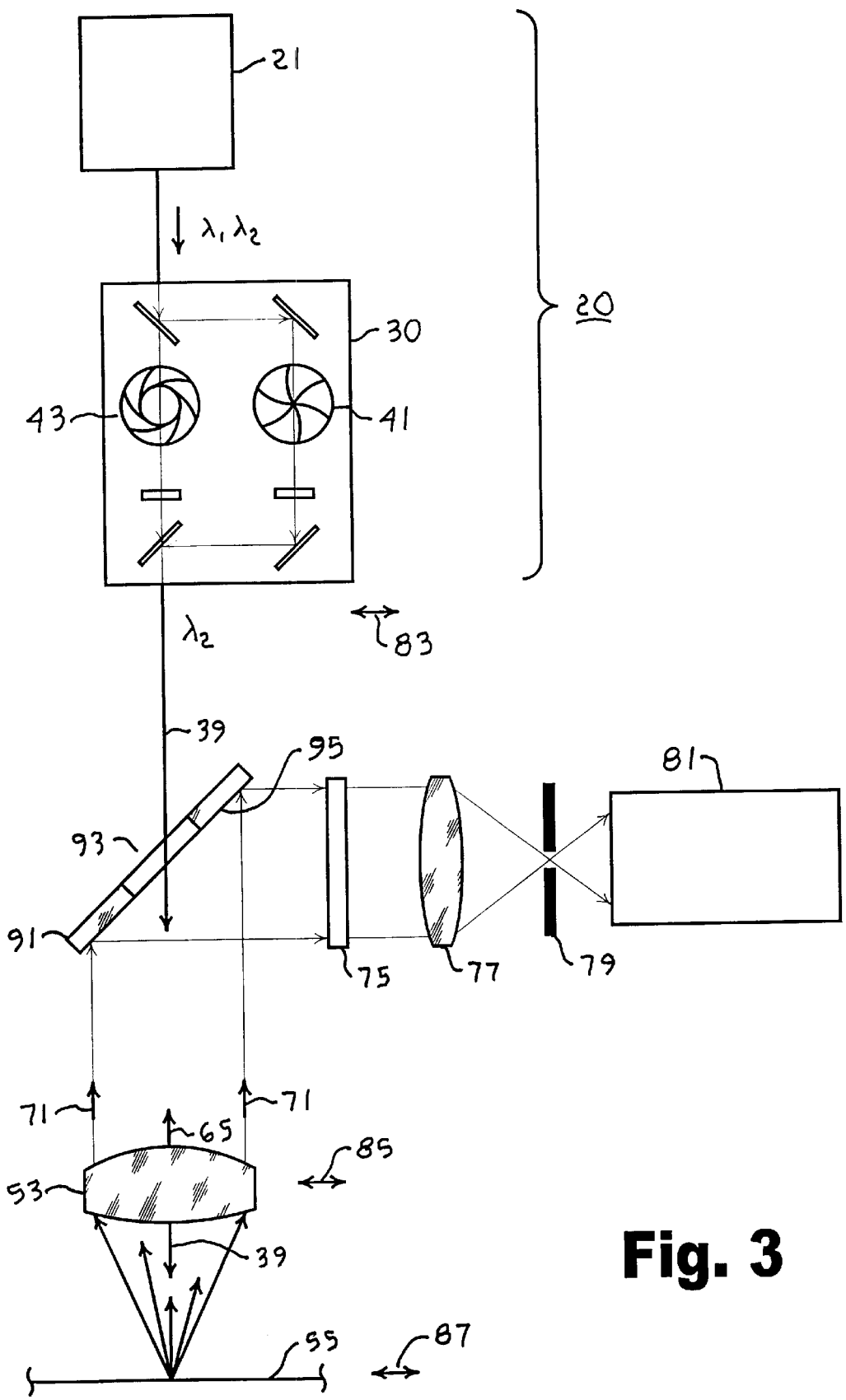
FIG. 3 is a diagrammatic illustration of an alternative embodiment of the imaging system of FIG. 1, comprising a mirror having a centrally-located opening, the mirror utilized for reflecting radiation emitted from a sample to a detector.

In an alternative embodiment, shown in FIG. 3, the excitation radiation 39 is 25 transmitted by the illumination head 20 to the surface of the sample 55 through a centrally-located opening 93 in an annular mirror 91. In the example provided, the excitation device 21 produces a radiation output having wavelengths $\lambda_1$ and $\lambda_2$. The excitation 93 has a wavelength of $\lambda_2$ as the first shutter 41 is closed and the second shutter 43 is open. Accordingly, the fluors of interest in the sample 55 produce an emission radiation 69 having a wavelength of $\lambda_{emit2}$. The opening 93 is positioned in the transmission paths of both the excitation radiation 39 and the specular reflection beam 65. The annular mirror 91 has a reflection surface 95 substantially reflective to radiation of wavelength $\lambda_{emit2}$. A portion of the composite emission beam 71 is reflected to the detector 81 by the annular mirror 91. Preferably, the width of the opening 93 is smaller than the width of the composite emission beam 71, and at least as large the diameter of the specular reflection beam 65. The opening 93 provides for most or all of the specular reflection beam 65 to pass back to the shutter assembly 30 rather than being transmitted to the detector 81.

In the present invention, the incident excitation radiation 39 is scanned across the surface of the sample 55 by any of three methods. In the first method, the shutter is assembly 30 is moved within the imaging system 10, as indicated by arrow 83. In the second method, the objective lens 53 is translated with respect to the surface of the sample 55, as indicated by arrow 85. In the third method, the sample 55 is laterally translated with respect to the imaging system 10, as indicated by arrow 87.

While the invention has been described with reference to particular embodiments, it will be understood that the present invention is by no means limited to the particular constructions and methods herein disclosed and/or shown in the drawings, but also comprises any modifications or equivalents within the scope of the claims.

What is claimed is:

1. An imaging system, suitable for use in optically scanning a sample, said imaging system comprising:
    a radiation device providing an excitation beam comprising radiation of at least wavelengths $\lambda_1$ and $\lambda_2$;
    an objective lens disposed between said radiation device and the sample;
    means for selecting one of said wavelengths for transmission through said objective lens such that said transmitted wavelength illuminates the sample, whereby a portion of said transmitted beam incident upon the sample is converted into and subsequently emitted as emitted radiation, said objective lens further disposed to substantially collimate at least a portion of said emitted radiation so as to form a corresponding emission beam directed away from the sample,
    a detector responsive to the wavelength of the emitted radiation, and
    a geometric beam splitter disposed in the transmission path of said excitation beam between said radiation device and said objective lens so as to provide at least a portion of said excitation beam in the direction of the sample, said geometric beam splitter further disposed in the transmission path of said emission beam and oriented so as to provide at least a portion of said excitation beam reflected from said sample and subsequently transmitted through said objective lens in the direction of said means for selecting and at least a portion of said emission beam transmitted through said objective lens in the direction of said detector based on the differences in the relative positions of said emission beam and said excitation beam at said geometric beam splitter.

2. The imaging system of claim 1 wherein said radiation device comprises a laser device.

3. The imaging system of claim 1 wherein said radiation device comprises a broadband radiation device.

4. The imaging system of claim 1 wherein said geometric beam splitter has a width at least as large as the width of said excitation beam.

5. The imaging system of claim 1 further comprising means for scanning said excitation beam across the sample.

6. The imaging system of claim 5 wherein said means for scanning comprises means for moving said excitation beam within said imaging system.

7. The imaging system of claim 5 wherein said means for scanning comprises means for translating said objective lens relative to the sample.

8. The imaging system of claim 5 wherein said means for scanning comprises means for translating the sample relative to said imaging system.

9. The imaging system of claim 1 wherein said objective lens comprises a focal length of approximately 6 millimeters.

10. The imaging system of claim 1 wherein said objective lens comprises a numerical aperture greater than 0.5.

11. The imaging system of claim 1 wherein said means for selecting comprises a shutter.

12. The imaging system of claim 1 further comprising filter means disposed in the transmission path of said emission beam, said filter means being substantially transmissive to the wavelength of the emitted radiation and substantially non-transmissive to radiation of at least wavelengths $\lambda_1$ and $\lambda_2$.

13. The imaging system of claim 1 wherein said detector comprises at least one member of the group consisting of a photo-multiplier tube, an avalanche photodiode, and a solid state optical detector.

14. An imaging system, suitable for use in optically scanning a sample, said imaging system comprising:
    a radiation device providing excitation beams comprising radiation of at least wavelengths $\lambda_1$ and $\lambda_2$;
    an objective lens disposed between said radiation device and the sample;
    means for selecting one of said excitation beams for transmission through said objective lens so as to illuminate the sample, a portion of said one of said excitation beams incident upon the sample being converted into and subsequently emitted as emission radiation, said objective lens further disposed to substantially collimate at least a portion of said emission radiation so as to form a corresponding emission beam transmitted away from the sample;
    a detector responsive to the wavelength of the emission radiation; and
    a geometric beam splitter disposed in the transmission path of said emission beam between said radiation device and said objective lens and oriented to provide at least a portion of said excitation beam reflected from the sample in the direction of said means for selecting and at least a portion of said emission beam in the direction of said detector based on the differences in the relative positions of said emission beam and said excitation beam at said geometric beam splitter.

15. The imaging system of claim 14 wherein said radiation device comprises at least one member of the group consisting of a dual wavelength laser device and a multiple-wavelength laser device.

16. The imaging system of claim 14 wherein said radiation device comprises a broadband radiation device.

17. The imaging system of claim 14 wherein said geometric beam splitter has a major dimension that is at least as large as the width of said emission beam.

18. The imaging system of claim 14 wherein said geometric beam splitter includes a centrally-located opening, said opening disposed within the transmission path of said emission beam such that at least a portion of said excitation beam reflected from the sample and passed through said objective lens passes through said opening.

19. The imaging system of claim 18 wherein the width of said opening is smaller than the width of said emission beam.

20. The imaging system of claim 14 further comprising means for scanning said excitation beam across the sample.

21. The imaging system of claim 14 further comprising filter means disposed in the transmission path of said emission beam, said filter means being substantially transmissive to radiation of at least one of wavelengths $\lambda_1$ and $\lambda_2$ and substantially non-transmissive to the wavelength of the emission radiation.

22. The imaging system of claim 14 wherein said detector comprises at least one member of the group consisting of a photo-multiplier tube, an avalanche photodiode, and a solid state optical detector.

23. An imaging system, suitable for use in optically scanning a sample, said imaging system comprising:

a radiation device providing excitation radiation of at least wavelengths $\lambda_1$ and $\lambda_2$;

an objective lens disposed between said radiation device and the sample;

means for selecting one of said wavelengths for transmission through said objective lens such that said transmitted wavelength is focused and illuminates the sample, whereby the sample subsequently emits emitted and said objective lens substantially collimates at least a portion of said emitted radiation so as to form a corresponding emission beam directed away from the sample, a detector responsive to the wavelength of the emitted radiation; and a geometric beam splitter disposed in the transmission path of said excitation radiation between said radiation device and said objective lens so as to provide at least a portion of said excitation radiation in the direction of said objective lens, said geometric beam splitter further disposed in the transmission path of said emission beam and oriented so as to provide at least a portion of said excitation beam reflected from said sample and subsequently transmitted through said objective lens in the direction of said means for selecting and at least a portion of said emission beam transmitted through said objective lens in the direction of said detector based on the differences in the relative positions of said emission beam and said excitation beam at said geometric beam splitter.

* * * * *